United States Patent
Li et al.

(10) Patent No.: US 7,745,372 B2
(45) Date of Patent: Jun. 29, 2010

(54) CATALYST FOR SELECTIVE HYDROGENATION OF OLEFINS AND ITS PREPARATION AS WELL AS USE

(75) Inventors: Mingfeng Li, Beijing (CN); Yang Chu, Beijing (CN); Yunjian Hu, Beijing (CN); Guofu Xia, Beijing (CN); Hong Nie, Beijing (CN); Yahua Shi, Beijing (CN); Dadong Li, Beijing (CN)

(73) Assignees: China Petroleum & Chemical Corporation, Beijing (CN); Research Institute of Petroleum Processing, SINOPEC, Beijing (CN)

( * ) Notice: Subject to any disclaimer, the term of this patent is extended or adjusted under 35 U.S.C. 154(b) by 1153 days.

(21) Appl. No.: 11/016,986

(22) Filed: Dec. 21, 2004

(65) Prior Publication Data
US 2005/0137434 A1 Jun. 23, 2005

(30) Foreign Application Priority Data
Dec. 22, 2003  (CN)  ......................... 2003 1 0121167
Mar. 31, 2004  (CN)  ......................... 2004 1 0029866

(51) Int. Cl.
B01J 23/00 (2006.01)
B01J 21/00 (2006.01)
B01J 20/00 (2006.01)

(52) U.S. Cl. ...................... 502/314; 502/315; 502/317; 502/322; 502/323; 502/327; 502/330; 502/332; 502/335; 502/337; 502/355; 502/415; 502/439

(58) Field of Classification Search ................ 502/314, 502/315, 317, 322, 323, 327, 330, 332, 335, 502/337, 355, 415, 439
See application file for complete search history.

(56) References Cited

U.S. PATENT DOCUMENTS

| | | | | | |
|---|---|---|---|---|---|
| 3,068,303 A | * | 12/1962 | Pattison | ...................... | 585/260 |
| 3,345,427 A | * | 10/1967 | Michaels et al. | ............ | 585/631 |
| 3,472,763 A | * | 10/1969 | Page et al. | .................. | 208/255 |
| 3,974,100 A | * | 8/1976 | Kubicek | ..................... | 502/241 |
| 4,025,561 A | * | 5/1977 | Suggitt et al. | ............... | 564/494 |
| 4,042,490 A | * | 8/1977 | Suggitt et al. | ............... | 208/264 |
| 4,066,574 A | * | 1/1978 | Tamm | ........................ | 502/220 |
| 4,607,055 A | * | 8/1986 | Grazioso et al. | ............ | 518/713 |
| 4,607,056 A | * | 8/1986 | Grazioso et al. | ............ | 518/714 |
| 4,616,040 A | * | 10/1986 | Grazioso et al. | ............ | 518/713 |
| 4,661,525 A | * | 4/1987 | Grazioso et al. | ............ | 518/714 |
| 4,774,220 A | * | 9/1988 | O'Young et al. | ............ | 502/314 |
| 4,837,193 A | * | 6/1989 | Akizuki et al. | ............... | 502/242 |
| 5,200,381 A | * | 4/1993 | Kamo | ........................ | 502/170 |
| 5,232,888 A | * | 8/1993 | Kamo | ........................ | 502/170 |
| 5,244,858 A | * | 9/1993 | Usui et al. | .................... | 502/220 |
| 5,258,347 A | * | 11/1993 | Khazai et al. | ............... | 502/306 |
| 5,268,512 A | * | 12/1993 | Miki et al. | .................. | 568/801 |
| 5,348,928 A | * | 9/1994 | Kukes et al. | ................. | 502/306 |
| 5,358,633 A | * | 10/1994 | Dai et al. | ................. | 208/216 R |
| 6,015,485 A | * | 1/2000 | Shukis et al. | ............... | 208/112 |
| 6,037,300 A | * | 3/2000 | Kasztelan et al. | ............ | 502/204 |
| 6,084,140 A | | 7/2000 | Kitamura et al. | | |
| 6,200,927 B1 | * | 3/2001 | Shukis et al. | ............... | 502/355 |
| 6,235,954 B1 | | 5/2001 | Wu et al. | | |
| 6,255,548 B1 | | 7/2001 | Didillon et al. | | |
| 6,388,162 B1 | | 5/2002 | Himelfard et al. | | |

FOREIGN PATENT DOCUMENTS

| | | |
|---|---|---|
| CN | 1113829 | 12/1995 |
| CN | 1047102 | 12/1999 |
| CN | 1302849 | 7/2001 |
| CN | 1101261 | 2/2003 |
| EP | 0693315 | 1/1995 |
| JP | 6-25020 | 2/1994 |
| KR | 2002-24713 | 4/2002 |

OTHER PUBLICATIONS

English language Abstract of CN1113829.
English language Abstract of CN1302849.
English language Abstract of CN1101261.
English language Abstract of CN1047102.
English language Abstract of JP 6-25020.
English language Abstract of Korean 2002-24713.

* cited by examiner

*Primary Examiner*—Cam N Nguyen
(74) *Attorney, Agent, or Firm*—Birch, Stewart, Kolasch & Birch, LLP

(57) ABSTRACT

A catalyst for the selective hydrogenation of olefins especially dienes, its preparation and use, said catalyst comprising an alumina support and cobalt and/or nickel selected from Group VIII, molybdenum and/or tungsten from Group VIB and alkali metal components supported on said support, characterized in that the catalyst contains 0.5-8% by weight of cobalt and/or nickel selected from Group VIII, 2-15% by weight of molybdenum and/or tungsten from Group VIB, over 2-8% by weight of alkali metals, and a balanced amount of alumina support calculated for oxides and based on the catalyst. Compared to the prior catalysts, the activity and selectivity for olefins especially dienes of the catalyst are higher when used in the hydrogenation of a gasoline distillate.

10 Claims, No Drawings

US 7,745,372 B2

CATALYST FOR SELECTIVE HYDROGENATION OF OLEFINS AND ITS PREPARATION AS WELL AS USE

FIELD OF THE INVENTION

The present invention relates to a hydrorefining catalyst, more particularly, to a catalyst for the selective hydrogenation of olefins especially dienes, its preparation and use.

BACKGROUND OF THE INVENTION

Catalytically cracked gasoline contains considerable dienes, which would also react with other hydrocarbons in catalytically cracked gasoline, in addition to the polymerization of itself, to form precursors of coke, gums at certain reaction temperatures. Generally, these dienes can be selectively removed by hydrogenation.

U.S. Pat. No. 6,084,140 discloses a process for preparing a catalyst for the selective hydrogenation of highly unsaturated hydrocarbons in olefin fractions. Said catalyst consists of alumina and metal palladium supported on said alumina. The content of metal palladium is 0.02-3.0% by weight. Said catalyst can effectively remove the highly unsaturated hydrocarbons in olefin fractions.

U.S. Pat. No. 6,255,548 discloses a process for preparing a catalyst for the selective hydrogenation of unsaturated hydrocarbons such as acetylenes and dienes. Said catalyst is prepared by supporting at least one metal of Group VIII and at least one assistant metal M on a support. The metal of Group VIII may be one or more of nickel, palladium, platinum, rhodium, ruthenium, and iridium, preferably palladium, nickel, and platinum with a content of 0.01-50% by weight, preferably 0.05-1% by weight for noble metals and 5-30% by weight for nickel. Metal M is selected from one or more of germanium, tin, gold, and silver with a content of 0.01-10% by weight, preferably 0.02-5% by weight. Said catalyst may also contain 0.1-3% by weight of alkali metals such as potassium or sodium and/or 0.01-2% by weight of sulfur element.

U.S. Pat. No. 6,388,162 discloses a process for removing dienes from olefin feed stocks. Said process removes dienes from feedstocks with carbon numbers between 10 and 20 and rich in olefins by refining. The catalyst used in said process consists of an alumina support and metal palladium supported on said alumina support with a metal content of 0.05-0.2% by weight, preferably 0.2% by weight, wherein the specific surface area of the alumina support is no larger than 15 m$^2$/g, preferably 2-5 m$^2$/g.

Use of a noble metal catalyst for selective hydrogenation can effectively remove dienes from feed oils. However, the noble metal catalyst easily deactivates when used to refine full or heavy fraction of catalytically cracked gasoline containing more sulfur and nitrogen, which limits the use of said catalyst.

In general, the hydrogenation of olefins especially dienes can easily proceed under hydrorefining conditions. However, when non-noble metal hydrorefining catalysts are used in selective hydrogenation to remove dienes from feed oils, the existing problem is how to avoid or reduce coking due to polymerization of olefins and saturation of monoolefins due to hydrogenation while ensuring the removal of dienes to enhance the stability and selectivity of hydrogenation.

CN 1113829A discloses a process for preparing a hydrorefining catalyst containing molybdenum, nickel and potassium metal components, the major character of which is that the catalyst is prepared by once impregnating a pre-shaped transient state alumina including η-, γ-, and θ-alumina, preferably γ-alumina in an ammonia-containing solution of molybdenum, nickel and potassium followed by drying and calcining. The contents of the metal components in said catalyst are 10.0-24.0% of $MoO_3$, 2.6-8.8% of NiO, 0.3-1.5% of K. Said catalyst can be used in the hydrodesulfurization of light oil fractions or gas containing organic sulfur, especially the hydrodesulfurization of straight-run gasoline and coked dry gas.

CN 1302849A discloses a protector of hydrogenation activity and its preparation, the support of which simultaneously contains γ- and δ-alumina. Said protector contains 3-22% by mole of oxides of Group VIB metals, 0.5-5% by mole of oxides of Group VIII metals, 0-2% by mole of Group IA elements, 0-3% by mole of Group VA elements and has a specific surface area of 100-250 m$^2$/g and a pore volume of 0.4-0.8 ml/g. The oxides of Group VIB metals in said protector are oxides of Mo and W; the oxides of Group VIII metals are oxides of Fe, Co, and Ni; and the Group VA elements are P, As, Sb, and Bi. Said catalyst is suitable for use as a protector of hydrotreating catalyst for heavy oils to remove metals and gums in feed oils.

The presence of alkali metals is favorable to inhibiting coking on the catalyst surface, but this kind of catalyst has low activity when used for the hydrogenation of dienes in gasoline fraction.

CONTENT OF THE INVENTION

The objective of the present invention is to provide a new catalyst for the selective hydrogenation of olefins especially dienes with both high activity and high selectivity.

Another objective of the present invention is to provide a new process for the selective hydrogenation of a distillate oil to remove olefins especially dienes.

A flirter objective of the present invention is to provide a process for preparing the new catalyst for the selective hydrogenation of olefins especially dienes with both high activity and high selectivity.

The present invention provides a catalyst for the selective hydrogenation of olefins especially dienes, which contains an alumina support and cobalt and/or nickel selected from Group VIII, molybdenum and/or tungsten from Group VIB and alkali metal components supported on said support, characterized in that the catalyst contains 0.5-8% by weight of cobalt and/or nickel selected from VIII Group, 2-15% by weight of molybdenum and/or tungsten from Group VIB, over 2-8% by weight of alkali metals, and a balanced amount of alumina support calculated for oxides and based on the catalyst.

The present invention provides a process for the selective hydrogenation of a distillate oil to remove olefins especially dienes, which comprises contacting a distillate oil with a catalyst under the hydrorefining condition, wherein said catalyst is the aforesaid catalyst provided by the present invention.

The catalyst provided by the present invention has high activity and selectivity for the hydrogenation of olefins especially dienes when used in the hydrorefining a distillate oil especially a gasoline distillate oil.

For example, when the hydrogenation of a heavy fraction of catalytically cracked gasoline with a diene number of 1.6 gI.(100 g)$^{-1}$ and a bromine number of 37.1 gBr. (100 ml)$^{-1}$ was conducted to remove dienes under the same reaction conditions, the diene number of the resulted oil was reduced to 0.3 gI.(100 g)$^{-1}$ and the bromine number was 36.1 gBr. (100 ml)$^{-1}$ if the catalyst of the present invention (with a nickel oxide content of 1.4% by weight, a molybdenum oxide content of 4.5% by weight and a potassium oxide content of 2.1% by weight) was used, while the diene number of the resulted oil was only reduced to 0.5 gI.(100 g)$^{-1}$ and the bromine number was only 34.7 gBr. (100 mil)$^{-1}$ if a catalyst (using, the same support as the present invention and having a nickel oxide content of 1.4% by weight, a molybdenum oxide content of 4.6% by weight and a potassium oxide content of 1.4% by weight) was used.

EMBODIMENT OF THE INVENTION

According to the catalyst provided by the present invention, a catalyst containing 1-65% by weight of cobalt and/or nickel selected from Group VIII, 4-12% by weight of molybdenum and/or tungsten from Group VIB, 2.5-6% by weight of alkali metals, and a balanced amount of alumina support calculated for oxides and based on the catalyst is preferred. The atom ratio of the Group VIII metal component to the Group VIB metal component prefers to be 0.5-2, and more preferably 0.7-1.5.

Said metal component of Group VIII is preferably nickel and said alkali metal is preferably potassium.

Said alumina support is selected from one or more of γ-, η-, θ-, δ-, and χ-alumina or one or more of γ-, η-, θ-, δ-, and χ-alumina containing at least one additive selected from the group consisting of silicon, titanium magnesium, boron, zirconium, thorium, niobium, and rare earths, preferably γ-alumina or γ-alumina containing at least one additive selected from the group consisting of silicon, titanium, magnesium, boron, zirconium, thorium, niobium, and rare earths.

Said alumina may be either a commodity or prepared by any process of the prior art. For example, it may be prepared by shaping and calcining one of trihydrated, monohydated and amorphous aluminas or their mixtures, or one of trihydrated, monohydrated and amorphous aluminas or their mixtures containing silicon, titanium, magnesium, boron, zirconium, thorium, niobium, and rare earths.

The process provided by the present invention for preparing the catalyst comprises contacting an alumina support with a solution containing cobalt and/or nickel selected from VIII Group, a solution containing molybdenum and/or tungsten from Group VIB and a solution containing alkali metal compounds under a condition sufficient to deposit cobalt and/or nickel selected from VIII Group, molybdenum and/or tungsten from Group VIB and alkali metal components, e g., impregnating said alumina support with a solution containing cobalt and/or nickel selected from VIII Group, a solution containing molybdenum and/or tungsten from Group VIB and a solution containing alkali metal compounds followed by drying and calcining. Cobalt and/or nickel selected from VIII Group, molybdenum and/or tungsten from Group VIB and alkali metals may be either simultaneously or separately incorporated into the alumina support.

Said molybdenum-containing compound is selected from one or more of molybdenum-containing soluble compounds such as one or more of molybdenum oxides, molybdates, and paramolybdates, with molybdenum oxide, ammonium molybdate, and ammonium paramolybdate therein being preferred.

Said tungsten-containing compound is selected from one or more of tungsten-containing soluble compounds such as one or more of tungstates, metatungstates, and ethyl metatungstates, with ammonium metatungstate and ammonium ethyl metatungstate therein being preferred.

Said cobalt-containing compound is selected from one or more of cobalt-containing soluble compounds such as one or more of cobalt nitrate, cobalt acetate, basic cobalt carbonate, cobalt chloride, and soluble complexes of cobalt, with cobalt nitrate and basic cobalt carbonate being preferred.

Said nickel-containing compound is selected from one or more of soluble compounds of nickel metal such as one or more of nickel nitrate, nickel acetate, basic nickel carbonate, nickel chloride, and soluble complexes of cobalt, with nickel nitrate and basic nickel carbonate being preferred.

Said alkali metal-containing compound is preferably selected from one or more of hydroxides, salts of inorganic acids or organic acids of alkali metals such as one or more of potassium hydroxide, potassium nitrate, potassium chloride, potassium acetate, potassium phosphate, potassium hydrogen phosphate, and potassium dihydrogen phosphate.

The catalyst provided according to the present invention may be shaped into various easily operated shapes such as microsphere, sphere, tablet, or strip, etc according to different objectives and requirements using conventional methods such as tableting, rolling, extruding, etc, which are well known to the skilled in the art.

According to the conventional method in the art, the catalyst provided by the present invention is generally pre-sulfurized with a sulfur-containing feed stock at a temperature between 140° C. and 370° C. in the presence of hydrogen before use. Such pre-sulfurization may be conducted outside the reactor or conducted in situ inside the reactor to convert the catalyst into the sulfide type.

According to the process provided by the present invention, said hydrorefining condition include a reaction temperature of 160-300° C., preferably 200-260° C., a hydrogen partial pressure of 1-6 MPa, preferably 1.2-4 MPa, a LHSV (liquid hourly space velocity) of 2-50 h$^{-1}$, preferably 5-30 h$^{-1}$, and a volume ratio of hydrogen to oil of 50-600, preferably 100-400.

The process provided by the present invention is particularly suitable for the hydrorefining a gasoline distillate oil to remove olefins especially dienes therein. Said gasoline distillate oil may be catalytically cracked gasoline, coked gasoline, straight-run gasoline, thermally cracked gasoline and their mixtures.

The present invention will be further described by the following examples. However, it should be understood that these examples are merely illustrative, but by no means restrictive to the present invention in any way.

Example 1

Description of the Catalyst Provided by the Present Invention and its Preparation 800 g of dry cement powder produced by the Catalyst Plant of Changling Refinery was extruded into cloverleaf pattern strips with a circumdiameter of 1.4 mm, then dried at 120° C. and calcined in air atmosphere at 630° C. for 3 hours, 584 g of support Z was obtained.

4 g of nickel nitrate, 6 g of ammonium molybdate, and 3.3 g of potassium hydroxide (with a KOH content of 82%, produced by Beijing Chemicals Plant, the same in the following description) were dissolved in 16% by weight of aqueous solution of $NH_3$ to prepare 90 ml of impregnation solution. 100 g of support Z was impregnated with the above impregnation solution for 4 hours, then dried at 120° C. for 4 hours and calcined at 420° C. for 4 hours. After cooling down to room temperature, the solid was impregnated again with 80 ml of aqueous solution containing 2 g of nickel nitrate, then dried at 120° C. for 4 hours and calcined at 420° C. for 4 hours, catalyst C1 was obtained. The contents of nickel, molybdenum, and potassium oxides in catalyst C1 are shown in Table 1.

The contents of nickel, molybdenum, and potassium oxides were measured by fluorescent X-ray spectroscopy (the same in the following).

Comparative Example 1

Description of a Reference Catalyst and its Preparation 4.0 g of nickel nitrate, 6 g of ammonium molybdate, and 2.2 g of potassium hydroxide were dissolved in 16% by weight of aqueous solution of $NH_3$ to prepare 90 ml of impregnation solution. 100 g of support Z was impregnated with the above impregnation solution for 4 hours, then dried at 120° C. for 4 hours and calcined at 420° C. for 4 hours, catalyst B1 was obtained. The contents of the nickel, molybdenum, and potassium oxides in catalyst B1 are shown in Table 1.

Comparative Example 2

Description of a Reference Catalyst and its Preparation 4.0 g of nickel nitrate, 6 g of ammonium molybdate, and 2.2 g of potassium hydroxide were dissolved in 16% by weight of aqueous solution of $NH_3$ to prepare 90 ml of impregnation solution. 100 g of support Z was impregnated with the above impregnation solution for 4 hours, then dried at 120° C. for 4 hours and calcined at 420° C. for 4 hours. After cooling down to room temperature, the solid was impregnated again with 80 ml of aqueous solution containing 2 g of nickel nitrate, then dried at 120° C. for 4 hours and calcined at 420° C. for 4 hours, catalyst B2 was obtained. The contents of nickel, molybdenum, and potassium oxides in catalyst B2 are shown in Table 1.

Example 2

Description of a Catalyst Provided by the Present Invention and its Preparation 4 g of nickel nitrate, 6 g of ammonium molybdate, and 9 g of potassium hydroxide were dissolved in 16% by weight of aqueous solution of $NH_3$ to prepare 90 ml of impregnation solution. 100 g of support Z was impregnated with the above impregnation solution for 4 hours, then dried at 120° C. for 4 hours and calcined at 420° C. for 4 hours. After cooling down to room temperature, the solid was impregnated again with 80 ml of aqueous solution containing 10 g of nickel nitrate, then dried at 120° C. for 4 hours and calcined at 420° C. for 4 hours, catalyst C2 was obtained. The contents of nickel, molybdenum, and potassium oxides in catalyst C2 are shown in Table 1.

Example 3

Description of a Catalyst Provided by the Present Invention and its Preparation 10 g of nickel nitrate, 14 g of ammonium molybdate, and 6.5 g of potassium hydroxide were dissolved in 16% by weight of aqueous solution of $NH_3$ to prepare 90 ml of impregnation solution. 100 g of support Z was impregnated with the above impregnation solution for 4 hours, then dried at 120° C. for 4 hours and calcined at 420° C. for 4 hours. After cooling down to room temperature, the solid was impregnated again with 80 ml of aqueous solution containing 14 g of nickel nitrate, then dried at 120° C. for 4 hours and calcined at 420° C. for 4 hours, catalyst C3 was obtained. The contents of nickel, molybdenum, and potassium oxides in catalyst C3 are shown in Table 1.

Example 4

Description of a Catalyst Provided by the Present Invention and its Preparation 800 g of SB aluminum hydroxide powder produced by CONDEA Co., Germany, was uniformly mixed with 750 ml of aqueous solution containing 115 g of magnesium nitrate [$Mg(NO_3)_2 \cdot 6H_2O$] and extruded into cloverleaf pattern strips with a circumdiameter of 1.4 mm, then dried at 120° C. and calcined in air atmosphere at 550° C. for 2 hours, 602 g alumina support Z2 containing 3.1% by weight of magnesium oxide was obtained.

7.5 g of nickel nitrate, 11 ml of ammonium metatungstate solution (79.3 g tungsten trioxide/100 ml solution), and 11.8 g of potassium nitrate were dissolved in 16% by weight of aqueous solution of $NH_3$ to prepare 90 ml of impregnation solution. 100 g of support Z2 was impregnated with the above impregnation solution for 4 hours, then dried at 120° C. for 4 hours and calcined at 420° C. for 4 hours, catalyst C4 was obtained. The contents of nickel, tungsten, and potassium oxides in catalyst C4 are shown in Table 1.

TABLE 1

| Example | Catalyst No. | Content, wt % | | | | Nickel/ molybdenum or tungsten (atom ratio) |
| --- | --- | --- | --- | --- | --- | --- |
| | | Nickel oxide | molybdenum oxide | Tungsten oxide | Potassium oxide | |
| 1 | C1 | 1.4 | 4.5 | | 2.1 | 0.6 |
| Comparative. Example 1 | B1 | 0.9 | 4.6 | | 1.4 | 0.4 |
| Comparative example 2 | B2 | 1.4 | 4.6 | | 1.4 | 0.6 |
| 2 | C2 | 3.1 | 4.3 | — | 5.4 | 1.4 |
| 3 | C3 | 5.5 | 10.5 | — | 4.1 | 1.0 |
| 4 | C4 | 1.7 | — | 7.9 | 5.0 | 0.7 |

Examples 5-6

Description of the Process of the Present Invention for the Selective Hydrogenation of a Distillate Oil to Remove Dienes The process of the present invention was used to conduct the selective hydrogenation of the heavy fraction of a catalytically cracked gasoline to remove dienes with a feed oil having properties shown in Table 2. The catalysts are C1 and C3 respectively. The particular process is crushing the catalyst to particles with diameters of 2-3 mm and loading 100 ml the catalyst into a 100 ml fixed-bed reactor. Before formal feeding, the catalyst was first sulfurized with a straight-run gasoline containing 2% by weight of carbon disulfide under the condition of a hydrogen partial pressure of 1.6 MPa, a temperature of 290° C., a LHSV of 2 $h^{-1}$, a hydrogen/oil volume ratio of 300, and a sulfurization time of 9 hours followed by switching to the feedstock to conduct reaction. After 100 hours of reaction, samples were taken for analysis. The hydrogenation conditions and product properties are shown in Table 3.

Determination of the diene number: 5 ml of sample was accurately sucked with a transfer pipet and dripped into a 5 ml ground-glass stoppered conical flask, whereto 20 ml of benzene-anhydrous maleic anhydride (1 liter of benzene contains 30 g of anhydrous maleic anhydride) and 0.2 ml of iodine-xylene solution (0.1 N) were accurately added with a transfer pipet, and a blank test was made at the same time using 10 ml of benzene to replace the sample. The conical flask was equipped with a ball reflux condenser and put in a thermostatic water bath of 80° C. to reflux for 30 min, then 5 ml of deionized water was added from the upper opening of the condenser and the reflux was continued for 30 min to fully hydrolyze the remaining maleic anhydride. The flask was cooled down to room temperature and the condenser was washed with 5 ml of ethyl ether and 20 ml of deionized water respectively. The conical flask was discharged and the mixture in the flask was poured into a 250 ml of separating funnel to conduct separation. Finally, the obtained separated aqueous solution was titrated with 0.5 N sodium hydroxide solution and the consumed volume was recorded.

Diene number=12.692×$N$×($B$−$A$)$L$×$d$ where:

N-concentration of the standard NaOH solution

B-volume of NaOH solution consumed in the blank test, ml

A—volume of NaOH solution consumed by the sample, ml

L-volume of the sample, d-density of the sample at 20° C., g/ml

The determination method of the bromine number was RIPP 66-90.

Comparative Examples 3-4

Reference catalysts were used to conduct the selective hydrogenation of the heavy fraction of a catalytically cracked gasoline to remove dienes and the properties of the feed oil are shown in Table 2. The catalysts were B1 and B2 respectively and the operation conditions were the same as Example 5. The properties of the product are shown in Table 3.

Examples 7-8

Description of the Process of the Present Invention for the Selective Hydrogenation of Distillates to Remove Dienes The process of the present invention was used to conduct the selective hydrogenation of the full fraction of a catalytically cracked gasoline to remove dienes and the properties of the feed oil are shown in Table 2. The catalysts are C2 and C4 respectively. The particular process is crushing the catalyst to particles with diameters of 2-3 mm and loading 100 ml the catalyst into a 100 ml of fixed-bed reactor. Before the formal feeding, the catalyst was first sulfurized with a straight-run gasoline containing 2% by weight of carbon disulfide under the condition of a hydrogen partial pressure of 1.6 MPa, a temperature of 290° C., a LHSV of 2 $h^{-1}$, a hydrogen/oil volume ratio of 300, and a sulfurization time of 9 hours followed by switching to the feedstock to conduct reaction. After 100 hours of reaction, samples were taken for analysis. The hydrogenation condition and product properties are shown in Table 3.

TABLE 2

| Oil | Heavy fraction of catalytically cracked gasoline | Full fraction of catalytically cracked gasoline |
|---|---|---|
| Density (20° C.), g/cm$^3$ | 0.7855 | 0.7149 |
| Sulfur, ppm | 1680 | 902 |
| Diene number, gI$_2$/100 g | 1.6 | 1.4 |
| Bromine number, gBr/100 g | 37.1 | 70.9 |
| distillation range, D-86, ° C. | | |
| Initial distillation point | 92 | 33 |
| 50% | 135 | 79 |
| Dry point | 190 | 180 |

TABLE 3

| | Example | | | | | |
|---|---|---|---|---|---|---|
| | Comparative example 3 | Comparative example 4 | 5 | 6 | 7 | 8 |
| Catalyst | B1 | B2 | C1 | C3 | C2 | C4 |
| partial pressure of hydrogen, MPa | 1.6 | 1.6 | 1.6 | 1.6 | 3.2 | 1.2 |
| Temperature, ° C. | 240 | 240 | 240 | 230 | 210 | 250 |
| LHSV, h$^{-1}$ | 20 | 20 | 20 | 20 | 8 | 30 |
| Hydrogen/oil volume ratio | 100 | 100 | 100 | 100 | 200 | 300 |
| Product property | | | | | | |
| Diene number, gI$_2$/100 g | 0.6 | 0.5 | 0.3 | <0.2 | 0.4 | <0.2 |
| Bromine number, gBr/100 g | 33.9 | 34.7 | 36.1 | 36.4 | 64.3 | 61.0 |

The feed oil, reaction conditions used in Comparative examples 3 and 4 were the same as in Examples 5 and 6 with an only difference in the composition of the applied catalysts. It can be seen from the results in Table 3 that the diene numbers of the products given by Examples 5 and 6 are obviously lower than those given by Comparative examples 3 and 4, demonstrating that the catalyst and its application method provided by the present invention have a higher hydrogenation activity for the hydrogenation of dienes.

The bromine number of the feed oil was 37.1 gBr/100 ml and the bromine numbers of the produced oils were somewhat lowered after hydrogenation. It can be seen from the results in Table 3 that the bromine numbers of the products given by Examples 5 and 6 were obviously higher than those given by Comparative examples 3 and 4, demonstrating that the catalyst and its application method provided by the present invention have higher selectivity for the diene removal reaction.

The present application claims priority under 35 U.S.C. §119 of Chinese Patent Application Nos. 200310121167.5 filed on Dec. 22, 2003 and 200410029866.1 filed on Mar. 31, 2004. The disclosure of the foregoing applications are expressly incorporated by reference herein in their entireties.

The invention claimed is:

1. A catalyst for the selective hydrogenation of olefins, wherein said catalyst contains an alumina support and cobalt and/or nickel from Group VIII, molybdenum and/or tungsten from Group VIB and alkali metal components supported on said support, wherein said catalyst contains 1.4-8% by weight of cobalt and/or nickel from Group VIII, 2-15% by weight of molybdenum and/or tungsten from Group VIB, greater than 2% by weight and less than or equivalent to 8% by weight of alkali metal components, and a balanced amount of alumina support calculated as oxides and based on the catalyst;

wherein the content of molybdenum and/or tungsten from Group VIB is greater than the content of cobalt and/or nickel from Group VIII.

2. The catalyst according to claim 1, wherein said olefins are dienes.

3. The catalyst according to claim 1, wherein said catalyst contains 1.4-6% by weight of cobalt and/or nickel from Group VIII, 4-12% by weight of molybdenum and/or tungsten from Group VIB, greater than 2.5% by weight and less than or equivalent to 6% by weight of alkali metal components, and balanced amount of alumina support calculated as oxides and based on the catalyst.

4. The catalyst according to claim 1, wherein said Group VIII metal component is nickel.

5. The catalyst according to claim 1, wherein said alkali metal component is selected from the group consisting of one or more of hydroxides, salts of inorganic or organic acids of alkali metals.

6. The catalyst according to claim 1, wherein said alkali metal is potassium.

7. The catalyst according to claim 6, wherein said metal component is selected from the group consisting of one or more of potassium hydroxide, potassium nitrate, potassium chloride, potassium acetate, potassium phosphate, potassium hydrogen phosphate, and potassium dihydrogen phosphate.

8. A process for preparing a catalyst for the selective hydrogenation of olefins, which comprises contacting an alumina support with a solution containing cobalt and/or nickel from Group VIII, a solution containing molybdenum and/or tungsten from Group VIB and a solution containing alkali metal components under conditions sufficient to deposit cobalt and/or nickel from Group VIII, molybdenum and/or tungsten from Group VIB and alkali metal components on said alumina support, followed by drying and calcining;

wherein said catalyst contains 1.4-8% by weight of cobalt and/or nickel from Group VIII, 2-15% by weight of molybdenum and/or tungsten from Group VIB, greater than 2% by weight and less than or equivalent to 8% by weight of alkali metal components, and a balanced amount of alumina support calculated as oxides and based on the catalyst;

wherein the content of molybdenum and/or tungsten from Group VIB is greater than the content of cobalt and/or nickel from Group VIII.

9. The process according to claim 8, wherein cobalt and/or nickel from Group VIII, molybdenum and/or tungsten from Group VIB and alkali metal components may be either simultaneously or separately incorporated into the alumina support.

10. The process according to claim 8, further comprising: pre-sulfurizing said catalyst.

* * * * *